(12) United States Patent
Cole et al.

(10) Patent No.: US 6,919,730 B2
(45) Date of Patent: Jul. 19, 2005

(54) CARBON NANOTUBE SENSOR

(75) Inventors: Barrett E. Cole, Bloomington, MN (US); David J. Zook, Golden Valley, MN (US)

(73) Assignee: Honeywell International, Inc., Morristown, NJ (US)

( * ) Notice: Subject to any disclaimer, the term of this patent is extended or adjusted under 35 U.S.C. 154(b) by 133 days.

(21) Appl. No.: 10/100,440

(22) Filed: Mar. 18, 2002

(65) Prior Publication Data

US 2003/0173985 A1 Sep. 18, 2003

(51) Int. Cl.$^7$ .................. G01R 31/00; G01R 27/08
(52) U.S. Cl. .................. 324/715; 324/96; 324/724
(58) Field of Search .................. 324/715, 724, 324/96, 721; 315/94; 240/236.1; 250/338.1; 374/120, 121, 132

(56) References Cited

U.S. PATENT DOCUMENTS

| | | | |
|---|---|---|---|
| 5,283,438 A | | 2/1994 | Dautriche ............... 250/338.3 |
| 6,046,485 A | | 4/2000 | Cole et al. ............... 257/428 |
| 6,140,045 A | * | 10/2000 | Wohlstadter et al. ......... 435/6 |
| 6,400,088 B1 | * | 6/2002 | Livingston et al. .......... 315/94 |
| 6,485,913 B1 | * | 11/2002 | Becker et al. ............. 435/6 |

OTHER PUBLICATIONS

Ajayan, P. M., "Nanotubes from Carbon", *Chem. Rev., 99*, American Chemical Society,(Jan. 5, 1999), 1787–1799.
CAO, A. , "Tandem Structure of Aligned Carbon Nanotubes on Au and its Solar Thermal Absorption", *Solar Energy Materials& Solar Cells*, vol. 70 (4), Elsevier Science Publishers, Amsterdam, NL,(Jan. 1, 2002), 481–486.
Kataura, H., et al., "Optical Properties of Singlewall Carbon Nanotubes", *Synthetic Metals*, vol. 103, Elsevier Sequoia, Lausanne, CH,(1999),2555–2558.
Kong, J. , et al., "Nanotube Molecular Wires as Chemical Sensors", *Science*, vol. 287, American Association for the Advancement of Science, US,(Jan. 28, 2000),622–625.
Varghese, O. K., et al., "Gas Sensing Characteristics of Multi–Wall Carbon Nanotubes", *Sensors and Actuators B*, vol. 81 (1), Elsevier Sequoia, S.A., Lausanne, CH,(Dec. 15, 2001),32–41.
Xu, J. M., "Highly Ordered Carbon Nanotube Arrays and IR Detection", *Infrared Physics & Technology*, vol. 42 (3–5), 1 Elsevier, NL 2 Workshop on Quantum Well Infrared Photodetectors, Dana Point, CA,(Jun.–Oct., 2001),485–491.
Collins, Philip. G.,et al., "Extreme Oxygen Sensitivity of Electronic Properties of Carbon Nanotubes", *Science*, v. 287, (Mar. 2000), 1801.
Dai, H.,et al., "Nanotube Molecular Wires as Chemical Sensors", *Science*, v. 287, (Jan. 2000),622.
Lee, S..M. ,et al., "Hydrogen Adsorption and Storage in Carbon Nanotubes", *Synthetic Metals*, v. 113, (2000),209.

\* cited by examiner

*Primary Examiner*—Anjan Deb
*Assistant Examiner*—John Teresinski
(74) *Attorney, Agent, or Firm*—Schwegman, Lundberg, Woessner & Kluth, P.A.

(57) ABSTRACT

Carbon nanotubes are formed on projections on a substrate. A metal, such as nickel is deposited on the substrate with optional platforms, and heated to form the projections. Carbon nanotubes are formed from the projections by heating in an ethylene, methane or CO atmosphere. A heat sensor is also formed proximate the carbon nanotubes. When exposed to IR radiation, the heat sensor detects changes in temperature representative of the IR radiation. In a gas sensor, a thermally isolated area, such as a pixel is formed on a substrate with an integrated heater. A pair of conductors each have a portion adjacent a portion of the other conductor with projections formed on the adjacent portions of the conductors. Multiple carbon nanotubes are formed between the conductors from one projection to another. IV characteristics of the nanotubes are measured between the conductors in the presence of a gas to be detected.

22 Claims, 5 Drawing Sheets

CARBON NANOTUBE SENSOR

FIELD OF THE INVENTION

The present invention relates to carbon nanotubes, and in particular to formation of sensors utilizing carbon nanotubes.

BACKGROUND OF THE INVENTION

Carbon nanotubes have been manufactured on substrates in a variety of different ways. Many methods of manufacturing carbon nanotubes involves the use of significant amounts of heat. This heat adversely affects semiconductor circuitry already formed on the substrate. Such circuitry exhibits further doping migration and other changes when its thermal budget is exhausted.

As the methods of manufacturing carbon nanotubes improves, more uses for them are being discovered. A further problem is obtaining selective growth patterns for the nanotubes to accomplish desired functions.

SUMMARY OF THE INVENTION

Carbon nanotubes are formed on projections on a substrate. A metal, such as nickel is deposited on the substrate, and heated to form the projections. Carbon nanotubes are formed from the projections by heating in an ethylene atmosphere. A heat sensor is also formed proximate the carbon nanotubes. When exposed to IR radiation, the heat sensor detects changes in temperature representative of the IR radiation.

In one embodiment, spaced platforms are first grown on the substrate, and the projections are formed on the platforms. Single wall carbon nanotubes are then grown from the projections to obtain a desired spacing. In further embodiments, milled $SiO_2$ surfaces are used to form the nanotubes. Other surfaces may also be used as discovered.

Carbon nanotubes are used in forming a gas sensor in a further embodiment. A thermally isolated area, such as a pixel is formed on a substrate with an integrated heater. A pair of conductors each have a portion adjacent a portion of the other conductor with projections formed on the adjacent portions of the conductors. Multiple carbon nanotubes are formed between the conductors from one projection to another. In one embodiment, the conductors comprise multiple interleaved fingers with carbon nanotubes spanning between them.

IV characteristics of the nanotubes are measured between the conductors in the presence of a gas to be detected. The gas absorbs into the nanotubes, changing their response to a voltage. In one embodiment, the heater is used to heat the nanotubes and drive off the gas, essentially resetting the nanotubes for further measurements.

In one embodiment, the nanotubes are formed by using the heater to heat the thermally isolated pixel in an ethylene, methane or CO atmosphere. In further embodiments, the nanotubes are formed using an external heater.

DETAILED DESCRIPTION OF THE INVENTION

In the following description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

Figure 1A:
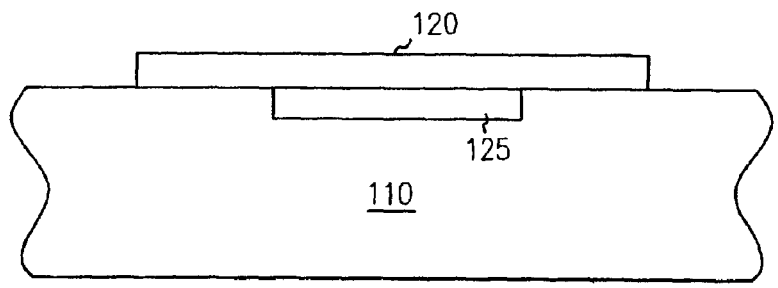
FIGS. 1A, 1B and 1C are progressive cross section representations of formation of an IR sensor.
Figure 1B:
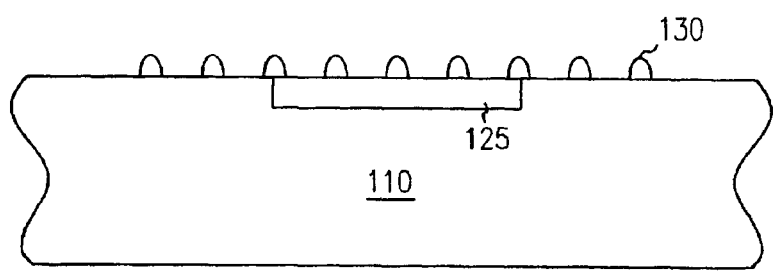
Figure 1C:
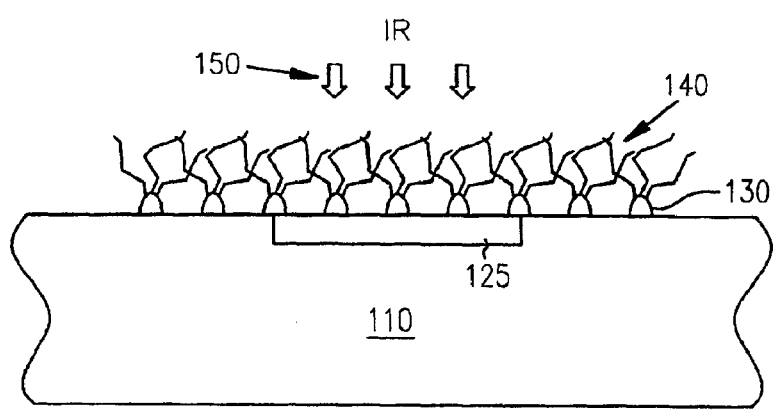

A process of forming a sensor is shown in FIGS. 1A–C. In FIG. 1A, a substrate 110 is formed of silicon or other suitable material, such as saphire or germanium or other substrate material which is acceptable for photolithographic processes. A first metallic layer 120 is formed on top of substrate 110. The metallic layer 120 is nickel or cobalt in one embodiment and is formed approximately 50 Angstrom thick in a well known manner. A temperature sensor 125 is formed of a material responsive to temperature changes, such as platinum, proximate to the metallic layer 120. In some embodiments, it is directly beneath the metallic layer, and in others, it is closely adjacent the metallic layer 120 such that it is responsive to temperature changes about the metallic layer. In various embodiments, the temperature sensor 125 is formed prior to or after formation of the metallic layer. A bolometer comprising a thermally isolated structure on a silicon nitride or oxide bridge is utilized in yet further embodiments.

The metallic layer is heated at approximately 900 degrees Celsius for several minutes until projections 130 form as shown in FIG. 1B. The time is temperature dependent, and other temperatures near or above a melting point of the metallic layer cause the metallic layer to separate into such projections in a known manner.

Once the projections are formed, the substrate is exposed to ethylene at approximately 700 to 800 degrees Celsius, forming carbon nanotubes 140 extending from the projections. Further embodiments utilize methane or CO. The nanotubes tend to grow in an undirected manner, resembling a tangle of hair upon completion. When exposed to infrared radiation (IR) 150, heat is trapped about the nanotubes 140 in a manner similar to that found in black gold structures. The heat causes a change in temperature that is detected by the temperature sensor 125. In one embodiment, the temperature sensor comprises a platinum resistance thermometer, and a change in resistance is measured corresponding to the change in temperature.

In one embodiment, a high fill factor of carbon nanotubes is utilized. The nanotubes are combined with the temperature sensor on a thermally isolated structure to measure temperature rise of the nanotube absorbed radiation. The nanotubes and temperature sensor are part of a pixel in one embodiment. Multiple pixels are formed close together, and the nanotubes are not in electrical contact with a pixel. They are formed on either a dielectric or isolated metal. The temperature sensor is also not in contact with the tubes. The temperature sensor may serve as a heater for formation of the nanotubes, or a separate heater or oven may be utilized.

One potential advantage of using a carbon nanotube structure as an IR absorber is that is provides high absorption, and also has a very low mass. This combination of properties enables fast pixel response times. Initial experimental carbon nanotube structures have demonstrated absorption rates of greater than 60% over a range of 3 to 14 um.

FIGS. 2A–D are cross section representations illustrating formation of a further sensor. In this embodiment, a substrate 210 has a first layer 220 formed, followed by a second layer 230. The first layer in one embodiment is platinum, or other layer having a higher melting point than the second layer 230. The second layer is nickel or cobalt, or other material one which carbon nanotubes will form. A temperature sensor 235 is formed proximate the first and second layers.

Figure 2A:
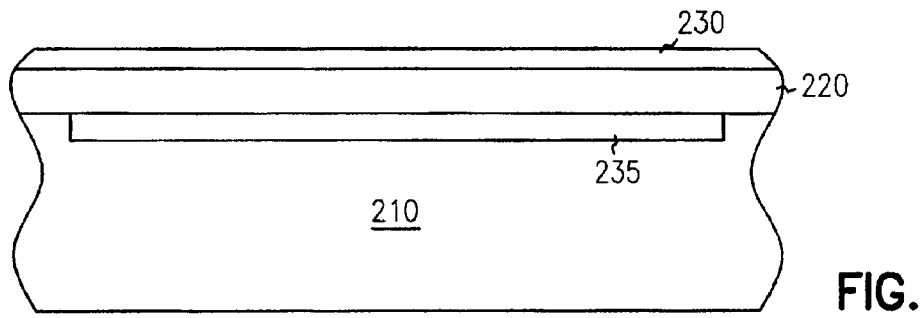
FIGS. 2A, 2B, 2C and 2D are progressive cross section representations of formation of an alternative IR sensor.
Figure 2B:
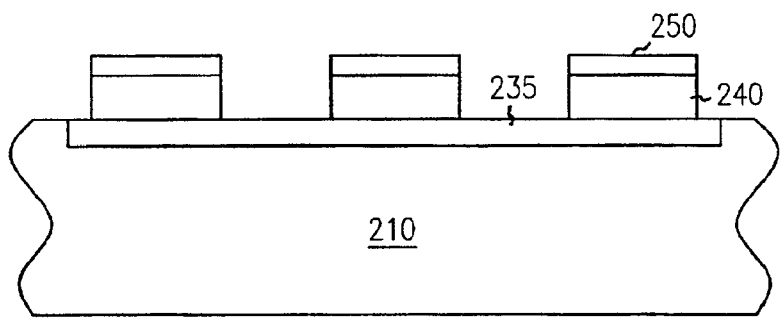
Figure 2C:
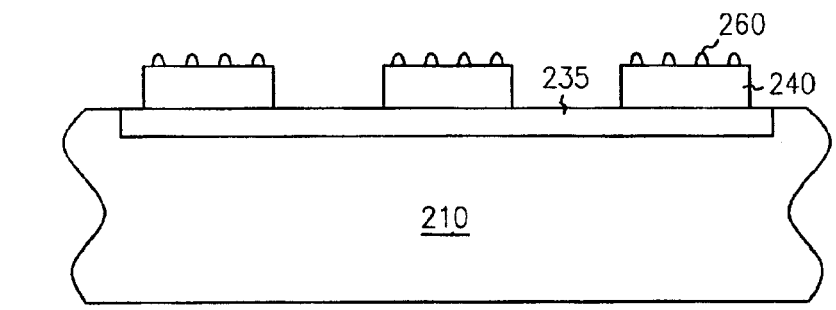

Using common photolithographic techniques, several islands or platforms are formed as shown in FIG. 2B. Each island is comprised of the first and second layers as earlier formed. Application of heat causes the formation of projections 260 out of the second layer material as shown in FIG. 2C. The resulting structures form a desired pattern of platforms or thin Ni islands ready for carbon nanotube growth. In one embodiment, the platforms are 1–5 micron rectangles, with a 1–5 micron spacing. Both the size and spacing, as well as the projection density are easily modified.

Figure 2D:
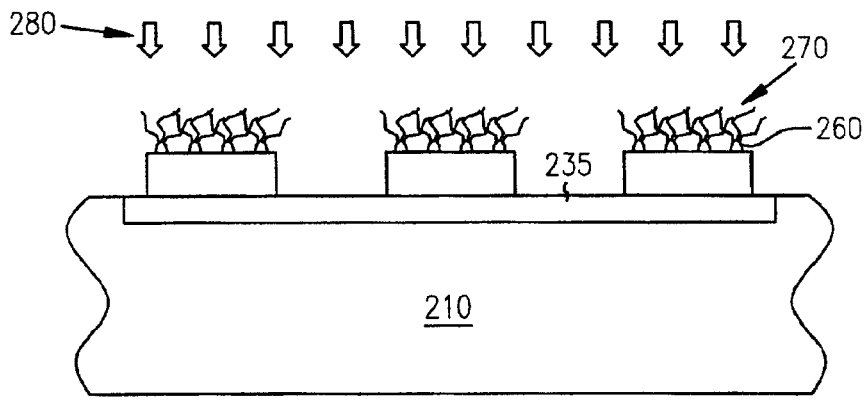

In FIG. 2D, following application of heat in an ethylene, methane or CO environment, nanotubes 270 have formed from the projections, again forming a tangle which traps heat produced by IR radiation 280. Four point temperature probes are used in one embodiment to ensure proper temperatures are maintained for nanotube deposition. By modifying the size and spacing of the platforms, the density of the projections, and the quantity of nanotubes formed, heat adsorption and trapping characteristics are modified.

In one embodiment, the nanotubes used to absorb IR radiation are on the order of, or smaller than the dimensions of the IR radiation, 3–12 um. Thus, the spacing of the projections 260 should be on the same order of size, or slightly closer to account for curvature of the nanotubes forming between them.

In further embodiments, nanotubes growth is promoted on milled $SiO_2$ surfaces or other surfaces yet to be determined. A fine photoresist patter is formed on a $SiO_2$ film and then milled into regions. The nanotubes grow where the milling of $SiO_2$ occurred.

Figure 3:
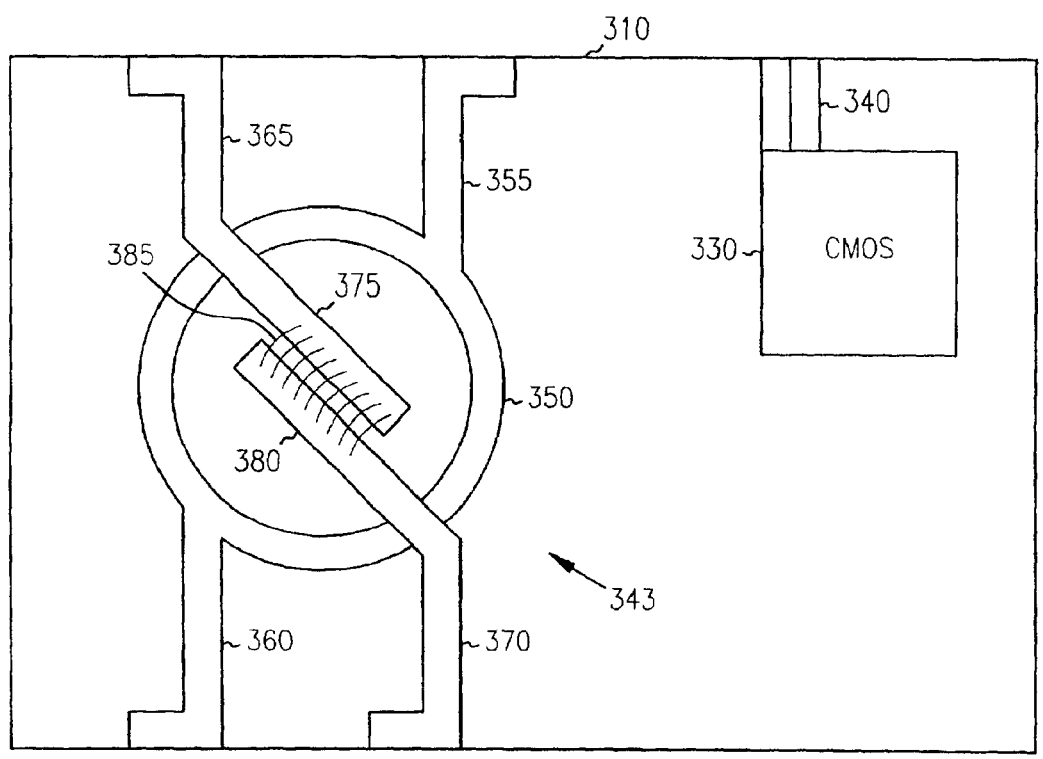
FIG. 3 is a planar block diagram view of a self-heating sensor having carbon nanotubes.

FIG. 3 is a planar block diagram view of a semiconductor substrate 310 having CMOS or other logic family circuitry 330 formed thereon. Conductors 340 are shown coupled to the circuitry 330 for connecting to further circuitry on or off the substrate. A sensor 343 is also integrated into the semiconductor substrate 310. The sensor 343 is formed in a manner which does not significantly adversely affect a thermal budget of the circuitry 330.

Sensor 343 is formed on a thermally isolated portion 345 of the substrate. The thermally isolated portion is formed in one of many known manners. In one embodiment, it resembles an inverse pyramid with air or insulator between it and most of the substrate. Points of contact with the substrate, such as at the peak of the pyramid and at other portions of the thermally isolated portion coupled by conductors to other circuitry or external contacts.

A heater 350, such as a platinum contact is formed proximate the thermally isolated portion in manner that enables the heater to heat the thermally isolated portion as desired. Two conductors 355 and 360 provide current to the heater to control the heat it produces. A pair of contacts 365 and 370 are formed, and extend onto the thermally isolated portion. The contacts overlap for at least a portion of their travel on the thermally isolated portion at overlapping portions 375 and 380. The overlapping portions 375 and 380 are adjacent to each other and run substantially parallel to each other in one embodiment. They are separated a short distance compatible with growth of carbon nanotubes 385 between them.

To form the carbon nanotubes, the heater heats the overlapping portions of the contacts in an ethylene, methane or CO environment. In one embodiment, projections are first formed, again using the heater to produce desired temperatures. In a further embodiment, platforms are formed on the overlapping portions of the contacts with projections formed on the platforms. An electric field is applied in one embodiment to control the direction of growth of the carbon nanotubes, and to obtain point to point connection by the tubes. This produces a structure of nanotubes stretching between overlapping portions 375 and 380 without significantly adversely heating circuitry 330.

Figure 4:
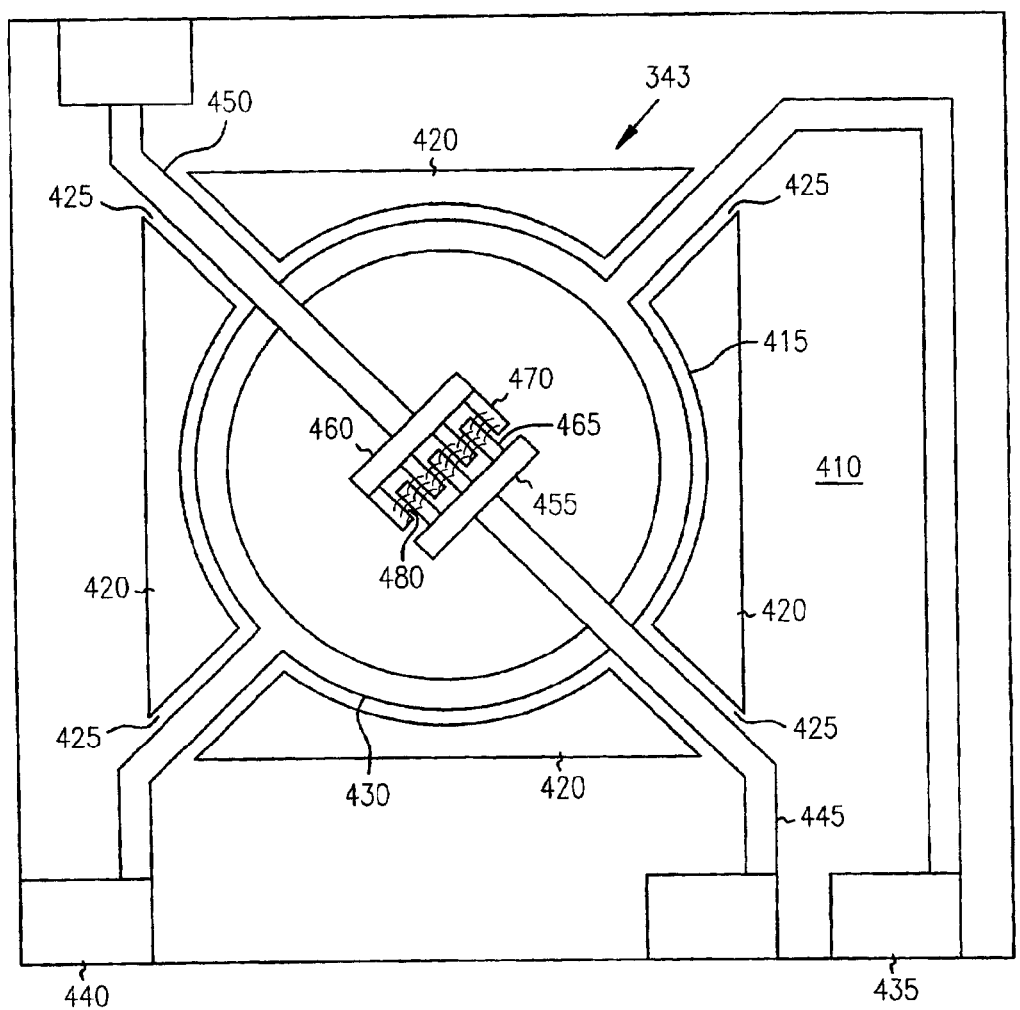
FIG. 4 is a planar block diagram view of a thermally isolated self-heating sensor having carbon nanotubes.

Further detail of one embodiment of sensor 343 is shown in FIG. 4. The sensor is formed in a substrate 410. A thermally isolated region 415 is formed in the substrate by creating air gaps 420 on all sides of the thermally isolated region 415 in a known manner. A pyramid shaped opening is formed, with the thermally isolated region supported by multiple supports 425. A heater 430 is formed on the thermally isolated region 415 in a circular pattern. The heater 430 comprises a platinum layer coupled to contacts 435 and 440. The platinum layer is formed on a Ni adhesion layer, and is passivated with SiN in one embodiment. Contacts 435 and 440 for heater 430 are supported by multiple supports bridging gaps 420 from substrate 410.

Further bridges 425 provide support for a pair of conductors 445 and 450 which extend onto the thermally isolated region 415. Conductor 445 and conductor 450 end in comblike adjacent conductor structures 455 and 460. Structure 455 has multiple fingers 465 intermeshing or interleaved with opposing fingers 470 from structure 460. The conductors are formed in a common manner such as by vapor deposition. The fingers are patterned in one embodiment using photolithographic techniques, or are formed by laser removal of the conductors to form a desired pattern. Plural carbon nanotubes 480 are formed from finger to finger by applying heat from heater 430 in an ethylene, methane or CO environment. An electric field is used in some embodiments to produce a more directed growth of the nanotubes between the fingers. Structures other than finger like structures that provide good characteristics for forming carbon nanotube bridges may also be used.

The sensor acts as a CO, O, or other gas sensor in one embodiment. IV characteristics between conductors 445 and 450 are measured. These characteristics change when the nanotubes 480 have absorbed CO. CO tends to stay absorbed in the nanotubes for several minutes or more. Without driving off the CO quickly, the sensor is slow to detect when CO levels have changed. The heater 430 is used to heat the nanotubes to a temperature sufficient to drive off the CO at a faster rate, yet not high enough to cause further growth of the nanotubes or otherwise significantly adversely affect the structure of the senor or other circuitry formed on the same substrate. When the CO is driven off, more CO is absorbed, allowing the sensor to be reused multiple times.

The use of an integrated heater on a thermally isolated structure allows the use of low power to desorb the gas. In further embodiments, external heaters are utilized.

Figure 5:
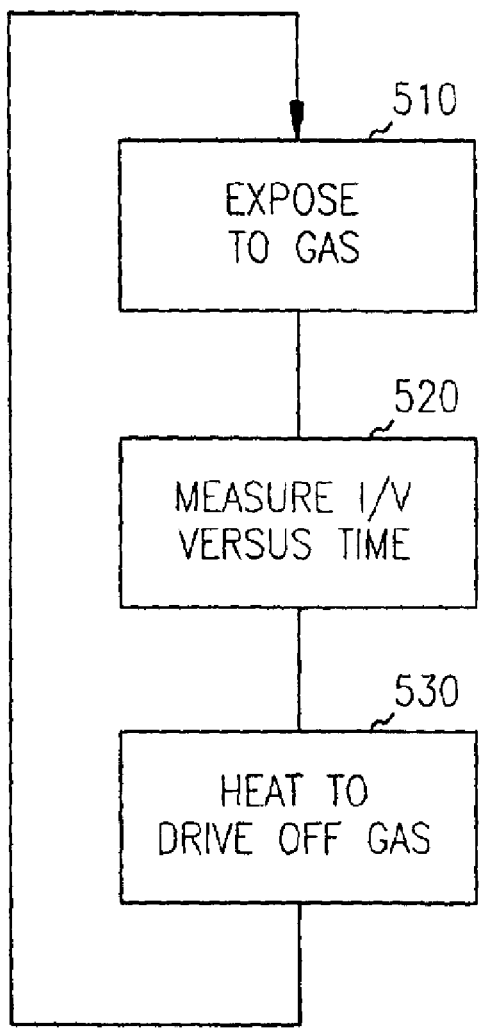
FIG. 5 is a flowchart showing the use of nanotubes as a gas sensor.

A flowchart in FIG. 5 illustrates use of the sensor to sense CO or other gases whose effect on carbon nanotubes IV characteristics are determinable. The sensor is exposed to gas at 510, and IV characteristics are measured versus time at 520. The sensor may be continuously exposed to gas, or the exposure may be halted at this point. At 530, the sensor is heated to approximately between 300 and 400 degrees Celsius to drive off the gas. Exposure to the gas is then continued or started again at 510. This cycle is repeated as many times as desired.

The electron affinity seems to vary depending on the gas being sensed. By mapping the IV responses of various known gases, the invention provides the ability to detect various gases.

If the sensor is powered by a battery, the sensor need not be operated until needed. When needed, a cleansing heating is first applied to make sure the carbon nanotubes are not already saturated with gas to be detected.

CONCLUSION

A method of forming carbon nanotubes has been described along with several uses of structures created with the nanotubes. The use of projections to control the density of the nanotubes provides the ability to better control temperature response of a plurality of nanotubes to radiation. The use of integrated heaters provides both the ability to form nanotubes without adversely affecting circuitry on the same die or substrate, but also to produce sensors that utilize heat to improve their cycle time, such as by driving off gas more quickly. While the nanotubes were described as forming in environments containing specific gases, they may be formed in different environments without departing from the invention.

What is claimed is:

1. An IR sensor comprising:
   a plurality of carbon nanotubes; and
   a temperature sensor positioned proximate the nanotubes for detecting heating caused by IR radiation falling on the nanotubes.

2. The IR sensor of claim 1 and further comprising a plurality of projections from a substrate, wherein the carbon nanotubes extend from the projections.

3. The IR sensor of claim 1 wherein the temperature sensor is integrated into the substrate.

4. The IR sensor of claim 2 wherein the temperature sensor is located below the carbon nanotubes.

5. The IR sensor of claim 1 wherein the carbon nanotubes are single wall carbon nanotubes.

6. The IR sensor of claim 1 wherein the carbon nanotubes are formed in a tangled manner.

7. A radiation sensor comprising:
   a substrate;
   a plurality of carbon nanotubes supported by the substrate; and
   a temperature sensor positioned thermally proximate the nanotubes for detecting heating caused by IR radiation falling on the nanotubes, wherein the nanotubes and sensor are thermally isolated from the substrate.

8. A method of sensing IR radiation, the method comprising:
   exposing a plurality of nanotubes supported by a substrate to IR radiation; and
   measuring the temperature proximate the nanotubes for detecting heating caused by IR radiation falling on the nanotubes.

9. An IR sensor comprising:
   a plurality of platforms formed on a substrate;
   a plurality of projections formed on each platform;
   carbon nanotubes formed on the projections; and
   a temperature sensor for detecting heating caused by IR radiation falling on the nanotubes.

10. The IR sensor of claim 9 wherein the temperature sensor is integrated into the substrate.

11. The IR sensor of claim 10 wherein the temperature sensor is located below the carbon nanotubes.

12. The IR sensor of claim 9 wherein the carbon nanotubes are single wall carbon nanotubes.

13. The IR sensor of claim 9 wherein the carbon nanotubes are formed in a tangled manner.

14. The IR sensor of claim 9 wherein the platforms are spaced between approximately 1 to 5 microns apart.

15. The IR sensor of claim 9 wherein the platforms are approximately 1–5 micron rectangle.

16. The IR sensor of claim 9 wherein the platforms are approximately 1–5 micron rectangles spaced between approximately 1 to 5 microns apart.

17. An IR sensor comprising:
    a substrate;
    a plurality of carbon nanotubes supported by the substrate, wherein the carbon nanotubes form a web such that heat produced from IR radiation falling upon the nanotubes is trapped in the web; and
    a temperature sensor positioned thermally proximate the nanotubes, such that a sensed temperature is representative of the IR radiation.

18. The IR sensor of claim 17 wherein the nanotubes and sensor are thermally isolated from the substrate.

19. The IR sensor of claim 17, wherein the web of nanotubes comprises nanotubes grown in an undirected manner.

20. The IR sensor of claim 19, wherein the nanotubes are tangled.

21. An IR sensor comprising:
    a plurality of platforms formed on a substrate;
    a plurality of projections formed on each platform;
    carbon nanotubes formed on the projections wherein the carbon nanotubes form a web such that heat produced from IR radiation falling upon the nanotubes is trapped in the web; and
    a temperature sensor proximate the carbon nanotubes for sensing temperature of the web that is representative of the IR radiation.

22. An IR sensor comprising:
    a plurality of platforms formed on a substrate;
    a plurality of projections formed on each platform;
    carbon nanotubes formed on the projections wherein the carbon nanotubes form a web such that heat produced from IR radiation falling upon the nanotubes is trapped in the web; and
    means for sensing temperature about the web, wherein the sensed temperatures is representative of the amount of IR radiation.

* * * * *